United States Patent

Messina et al.

[11] Patent Number: 4,792,637
[45] Date of Patent: Dec. 20, 1988

[54] PROCESS FOR THE PREPARATION OF VINYL ETHERS

[75] Inventors: Giuseppe Messina, Alghero; Mario D. Moretti, Sassari; Salvatore R. Sanna, Sorso; Giovanni Soma; Pier G. Cabras, both of Sassari, all of Italy

[73] Assignee: Enichem Anic SpA, Palermo, Italy

[21] Appl. No.: 74,560

[22] Filed: Jul. 17, 1987

[30] Foreign Application Priority Data

Jul. 30, 1986 [IT] Italy .................. 21313 A/86
Dec. 18, 1986 [IT] Italy .................. 22745 A/86

[51] Int. Cl.$^4$ .................. C07C 41/01; C07C 41/28
[52] U.S. Cl. .................. 568/626; 568/592; 568/594; 568/667; 568/687; 568/691; 568/654; 568/663; 558/379
[58] Field of Search .............. 568/687, 654, 626, 663, 568/667, 583, 691; 558/379

[56] References Cited

U.S. PATENT DOCUMENTS 2,566,415  9/1951  Hoaglin et al. .................. 568/687

FOREIGN PATENT DOCUMENTS 681059  10/1952  United Kingdom .

*Primary Examiner*—Howard T. Mars
*Attorney, Agent, or Firm*—Hedman, Gibson, Costigan & Hoare

[57] ABSTRACT

A process for the synthesis of vinyl ethers of formula

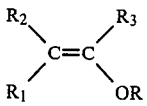

wherein $R_1$ and $R_2$, each independently, represent hydrogen or a primary, secondary or tertiary alkyl group, $R_3$ is a hydrogen, a primary alkyl, phenyl, or substituted phenyl group, or $R_2$ and $R_3$, taken together, represent a polymethylene chain containing from 3 to 10 carbon atoms wherein one or more hydrogens can be replaced by methyl or ethyl groups, and R is a primary, secondary or tertiary alkyl group, which comprises reacting a suitably selected dioxolane derivative of formula II

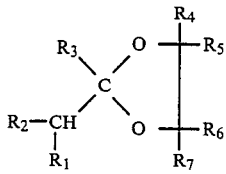

wherein $R_1$, $R_2$, and $R_3$ are as defined above, and $R_4$, $R_5$, $R_6$, and $R_7$, each independently, represent hydrogen or an alkyl group, with a boric acid ester of formula III

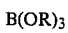

wherein R is as defined above, in the vapor phase, at a temperature comprised between 100° and 400° C., and in the presence of an acidic heterogeneous catalyst.

14 Claims, No Drawings

PROCESS FOR THE PREPARATION OF VINYL ETHERS

The present invention refers to a new process for the synthesis of vinyl ethers. More particularly, the present invention relates to a process for preparing a vinyl ether of general formula I

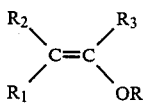    I wherein
- $R_1$ and $R_2$, each independently, represent hydrogen or a primary, secondary or tertiary alkyl group,
- $R_3$ is hydrogen, a primary alkyl, phenyl, or substituted phenyl group, or
- $R_2$ and $R_3$, taken together, represent a polymethylene chain containing from 3 to 10 carbon atoms wherein one of more hydrogens can be replaced by methyl or ethyl groups, and
- R is a primary, secondary or tertiary alkyl group, which comprises reacting a suitably selected dioxolane derivative of formula II

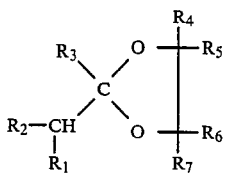    II wherein
- $R_1$, $R_2$, and $R_3$ are as defined above, and
- $R_4$, $R_5$, $R_6$, and $R_7$, each independently, represent hydrogen or an alkyl group, with a boric acid ester of formula III

 $B(OR)_3$    III wherein
R is as defined above,
in the vapor phase, at a temperature comprised between 100 and 400° C., and in the presence of an acidic heterogeneous catalyst.

For the purposes of the present invention, the term "alkyl radical" designates a straight or branched alkyl radical containing from 1 to 10 carbon atoms. The term "substituted phenyl" identifies a phenyl radical bearing 1 to 3 substituents which may be the same or different, must be inert toward boric acid esters and should permit vaporization of the starting dioxolane of formula II at a temperature below 400° C. Suitable substituents are for instance lower alkyl groups, preferably methyl or ethyl, lower alkoxy groups, preferably methoxy or ethoxy, halogen atoms, preferably chlorine atoms, nitro, cyano, tri-fluoromethyl, lower-alkyl-carbonyl, and lower-alkoxy-carbonyl groups, and the like substituents.

Vinyl ethers are chemical compounds well known in the open and patent literature which find many and interesting applications in homo- and co-polymerization processes as well as in the synthesis of several products of commercial significance (see for instance "High polymers"—Volume 24 entitled "Vinyl and Diene Monomers", Ed. E.C.Leonard—Part 1 —Chapter 7—Vinyl Ethers—Wiley-Interscience Publ. (1970)).

A number of different synthetic approaches to vinyl ethers are known in literature. However the processes of commercial importance are only the following ones:

(a) treatment of the respective alcohols with acetylene or higher acetylenes under high pressures (10–30 atm), at a temperature comprised between 150° and 200° C. and in the presence of a strong base (alkali metals or hydroxides may be used or the alkali alcoholate may conveniently be employed). Precautions for insuring safety at the high pressure required for acceptable reaction rates must be taken. It should be borne in mind in fact that acetylene derivatives can easily give rise to uncontrolled reactions; and (b) thermal cracking of acetals in the presence of platinum group metals; this method however cannot be employed for the synthesis of vinyl ethers from ketone acetals (ketals) because of the known difficulties in preparing these compounds.

It has now surprisingly been found that it is possible to prepare vinyl ethers of formula I, including also those compounds wherein $R_3$ is a primary alkyl group, in high yields, through vapor-phase reaction of a cyclic acetal or ketal of formula II and a boric acid ester of formula III, in the presence of an acidic heterogeneous catalyst.

The process of the present invention is actually carried out by blowing a gaseous mixture of the two reaction partners of formulas II and III over a catalyst consisting of one or more acidic oxides.

The heterogeneous catalyst which can suitably be employed in the process of the present invention is one of the so-called solid acidic oxides, generally named as chalcides : said group includes alumina, silica, and the mixtures of alumina and silica, either natural or synthetic, in which other oxides such as chromia, magnesia, boria, molybdena, thoria, zirconia, etc. may so be present, as well as molybdenum sulfide (see to this purpose Friedel-Crafts Chemistry—Wiley—Interscience Publisher—(1973)—pp.343-55).

Among the above mentioned compounds, alumina in its various forms and the diatomaceous earths generally used as catalysis supports or chromatography fillers, such as dicalite, celite, chromosorb, etc., proved to be particularly useful as the reaction catalyst.

Good results are obtained by using the above products previously activated at temperatures comprised between 200° and 1300° C. Also good results are obtained by using catalytic compositions obtained by wet-coating one of the above mentioned oxides or oxide mixtures with boric acid, followed by its activation at temperatures comprised between 200° and 600° C.

The vapor-phase process of the present invention operates with a dioxolane-to-boric-acid-ester molar feed ratio of between 10:1 and 0.5:1. As the reaction rate does not vary to a great extent with trialkylborate concentration, according to a preferred embodiment of the present invention, a high dioxolane-to-boric-acid-ester molar ratio is employed as the almost complete conversion of the trialkylborate can thus be achieved.

As an example, 3:1 dioxolane-to-boric-acid-ester molar ratio affords % conversions of the starting dioxolane of formula II comparable to those which can be obtained with lower molar ratios but it brings about the almost complete conversion of the boric acid ester of formula III. The optimum range, as far as the molar ratio between the reactants is concerned, is therefore comprised between 5:1 and 1:1.

Operating temperatures and pressures are those which allow contacting of the reactants with the catalyst in the vapor phase. In general, temperatures comprised between 100° and 400° C. proved to be particularly useful to this purpose. A preferred temperature range is however comprised between 180° and 280° C., and a most preferred range is between 200° and 250° C.

At a temperature lower than 180° C. the reaction rate is in fact much lower, while at temperatures higher than 280° C., a higher % conversion but a lower selectivity is obtained. At a temperature higher than 280° C., in fact, also the reaction rates of some undesired side-reactions steadily increase. The most important of said side-reactions is the condensation of two alcohol hydroxy groups to give a glycol- or di-alkyl ($R_2O$) ether. Water which forms in this side-reaction combines with the obtained vinyl ether affording the starting carbonyl compound and alcohol, and considerably lowering the overall yields. As it has been found that this side-reaction can be depressed lowering the reaction temperature, it is therefore advisable—in order to optimize the process—to carry out the process at the lowest temperature which still provides for an acceptable reaction rate.

The reaction may conveniently be carried out under atmospheric pressure, however higher or lower pressure values may as well be applied provided the reaction temperature is such that passing of the reactants over the catalyst occurs in the vapor phase. The reaction, like all the vapor-phase catalytic reactions, is preferably carried out by blowing a gaseous mixture of the reactants over the catalyst in the suitably selected operating conditions and collecting the exit stream.

More particularly, optimum results have been obtained with a contact time of the reactants with the catalyst comprised between 10 and 600 sec. The longer the contact time, the higher is the conversion of the reactants; thus, working at 200° C. and with a molar ratio of 1, it is possible to get the almost complete conversion of the reactants with a contact time of 2–4 minutes, while with a contact time of 1 minute a conversion of about 40% is obtained.

The reaction may also be carried out blowing over the catalyst a gaseous mixture which contains, in addition to the reactants, also a carrier. Said carrier should be selected from the low-boiling inert organic compounds, such as for instance the aliphatic or aromatic hydrocarbons e.g. pentane, hexane, cyclohexane, benzene, and the like, or the corresponding alkanols ROH wherein R has the same meaning as in the starting boric acid ester. The reaction between the cyclic ketal or acetal and the boric acid ester mainly involves the exchange between the dioxolane glycol moiety and the boric acid ester alcohol moiety, to give a mixture of products essentially consisting of the desired vinyl ether of formula I, the alcohol ROH, and mixed boric esters containing both glycol and alkoxy residues.

As for the obtained mixed boric acid esters, the main product of the reaction of a dioxolane II and a tri-alkyl borate III is a boric acid ester of formula IV

This compound, can be easily separated from the other reaction products, and reacted with the alcohol ROH to afford the starting trialkylborate III, which can be recycled as such, and the glycol V

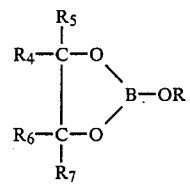

which can be converted into the dioxolane II and then recycled.

Furthermore, both the boric acid esters of formula IV and the glycols of formula V are compounds of commercial significance. In particular, the boric acid ester of formula IV wherein R represents a methyl group and $R_4$, $R_5$, $R_6$, and $R_7$ are hydrogen, is useful as fuel additive.

At the end of the reaction, the exit stream is collected and partially condensed in order to perform a preliminary rough separation between the higher boiling compounds which condensate and the lower boiling ones which remain in the vapor phase. These last ones are separately condensed and separated by distillation. The unreacted starting compounds are recycled while, if desired, the thus obtained product of formula I is further purified by means of conventional purification techniques well known to the ordinarily skilled chemist, such as chromatography, solvent extraction, distillation techniques, etc.

Separation of the alcohol/trialkylborate azeotrope is, however, not strictly required because, as already pointed out, the process of the present invention can also be carried out by feeding the reactor with a gaseous mixture containing also substantial amounts of a carrier, such as for instance an alcohol with the same alkoxy residue of the starting boric acid ester. Therefore, the azeotrope can be recycled as such.

The cyclic acetals and ketals employed as starting materials in the process of the present invention can be easily synthetised by known literature methods, e.g. by reacting aldehydes or ketones with oxiranes or glycols in the presence of acidic catalysts. Also the boric acid esters III can be easily prepared starting from boric acid or boric anhydride and the alcohol ROH or by transesterification of conventional boric acid esters with the alcohol ROH.

The process of the present invention offers the following advantages over the above cited prior art processes :

it does not share the safety problems of the method which involves treatment of the alcohols with acetylenes;

the starting compounds, unlike the higher acetylenes such as methylacetylene, ethylacetylene etc., are easily available;

unlike thermal cracking of acetals, it may be used also for the synthesis of vinyl ethers starting from ketones;

it allows preparation of all the desired vinyl ethers from a common dioxolane starting compound, just suitably selecting the trialkylborate reaction partner.

The following examples better illustrate the process of the present invention without representing a limitation to the scopes thereof.

EXAMPLE 1

$Al_2O_3$ pellets, 2 to 5 mm in diameter, (100 g) are soaked with an aqueous solution containing $H_3BO_3$ (25 g). Water is slowly evaporated off, the residue is dried in the oven at 120° C. and then calcined at 400° C. for 4 hours. The thus obtained catalyst (100 ml corresponding to 73 g) is poured into a jacketed tubular reactor ($\phi i=1''$; h=25 cm). The temperature is brought to 200° C. and a mixture consisting of

| | |
|---|---|
| trimethylborate | 33.65% |
| 2,2-dimethyl-1,3-dioxolane | 66.35% | is continuously passed over the catalyst with a flow rate of 35 g/h.

The vaporized charge is pre-heated to the reaction temperature before entering the reactor. The exiting vapor has the following composition:

| | |
|---|---|
| dimethylether | 0.62% w. |
| methanol | 6.12% w. |
| acetone | 0.78% w. |
| 2-methoxy-propene | 13.78% w. |
| trimethylborate | 11.49% w. |
| 2,2-dimethoxypropane | 0.92% w. |
| 2,2-dimethyl-1,3-dioxolane | 44.55% w. |
| 2-methoxy-1,3,2-dioxaborolane | 21.72% w. |

Trimethylborate and 2,2-dimethyl-1,3-dioxolane % conversion of 65.85% and 32.83% respectively.

Selectively in 2-methoxy-propene is 89.59% calculated on the converted dioxolane.

EXAMPLE 2

After 2 hours running of the catalyst of example 1, 35 g/h of a mixture consisting of:

| | |
|---|---|
| trimethylborate | 24.1% w. |
| 2,2-dimethyl-1,3-dioxolane | 75.9% w. | is passed through the reactor, in the vapor phase, at 200° C. The effluent which is obtained has the following composition:

| | |
|---|---|
| dimethylether | 0.34% w. |
| methanol | 7.03% w. |
| acetone | 0.43% w. |
| 2-methoxy-propene | 15.83% w. |
| trimethylborate | 0.22% w. |
| 2,2-dimethoxypropane | 0.31% w. |
| 2,2-dimethyl-1,3-dioxolane | 52.42% w. |
| 2-methoxy-1,3,2-dioxaborolane | 23.42% w. |

Trimethylborate and 2,2-dimethyl-1,3-dioxolane % conversion is 99.1% and 30.93% respectively.

Selectivity in 2-methoxy-propene, based on the converted dioxolane, is 95.48%. EXAMPLE 3

After about 40 hours running of the catalyst of the foregoing example, a gaseous mixture consisting of:

| | |
|---|---|
| trimethylborate | 50.42% w. |
| 2,2-dimethyl-1,3-dioxolane | 49.58% w. | is blown through the reactor with a flow rate of 40 g/h at 200° C. The effluent which is obtained has the following composition:

| | |
|---|---|
| dimethylether | 0.65% w. |
| methanol | 5.92% w. |
| acetone | 0.82% w. |
| 2-methoxy-propene | 13.32% w. |
| trimethylborate | 29.39% w. |
| 2,2-dimethoxypropane | 0.37% w. |
| 2,2-dimethyl-1,3-dioxolane | 28.9% w. |
| 2-methoxy-1,3,2-dioxaborolane | 20.63% w. |

Trimethylborate and 2,2-dimethyl-1,3-dioxolane % conversion is 41.7%.

Selectivity in 2-methoxy-propene, based on the converted dioxolane, is 91.21%.

EXAMPLE 4

$Al_2O_3$ pellets (100 ml corresponding to 73 g) 2÷5 mm in diameter, previously activated at 400° C. for 4 hours, are charged into a jacketed tubular reactor.

The temperature within the reactor is brought to 200° C. and trimethylborate, vaporized at the same temperature, is fed from the top to the bottom of the reactor with a flow rate of 50 g/h.

The exiting vapor contains trimethylborate and substantial amounts of methanol produced in the reaction of trimethylborate with alumina hydroxy groups. Methanol formation and boron absorption by the catalyst subsides after 2 hours.

A gaseous mixture of:

| | |
|---|---|
| trimethylborate | 49.67% w. |
| 2,2-dimethyl-1,3-dioxolane | 50.33% w. | pre-heated to 200° C. is then passed through the reactor with a flow rate of 35 g/h. The exit stream has the following composition:

| | |
|---|---|
| dimethylether | 0.28% w. |
| methanol | 6.81% w. |
| acetone | 0.35% w. |
| 2-methoxy-propene | 15.61% w. |
| trimethylborate | 26.13% w. |
| 2,2-dimethoxypropane | 0.60% w. |
| 2,2-dimethyl-1,3-dioxolane | 27.19% w. |
| 2-methoxy-1,3,2-dioxaborolane | 23.09% w. |

Trimethylborate and 2,2-dimethyl-1,3-dioxolane conversion is 47.38% and 46.32% respectively.

Selectivity in 2-methoxy-propene is 94.84% of the converted dioxolane.

EXAMPLE 5

A mixture consisting of:

| | |
|---|---|
| trimethylborate | 63.5% w. |
| 2,2-dimethyl-1,3-dioxolane | 36.5% w. | vaporized at 200° C., is continuously passed, with a flow rate of 35 g/h, over the catalyst described in example 4, after 40 hours running. The effluent which is obtained has the following composition:

| | |
|---|---|
| dimethylether | 0.36% w. |
| methanol | 4.76% w. |
| acetone | 0.45% w. |
| 2-methoxy-propene | 10.71% w. |
| trimethylborate | 47.18% w. |
| 2,2-dimethoxypropane | 0.08% w. |
| 2,2-dimethyl-1,3-dioxolane | 20.45% w. |
| 2-methoxy-1,3,2-dioxaborolane | 16.01% w. |

Trimethylborate and 2,2-dimethyl-1,3-dioxolane % conversion is 43.96% and 42.57%, respectively.

EXAMPLE 6

After 70 hours running of the same catalyst, a mixture consisting of:

| | |
|---|---|
| trimethylborate | 33.72% w. |
| 2,2-dimethyl-1,3-dioxolane | 66.28% w. | is fed to the reactor, vaporized at 200° C., with a flow rate of 35 g/h.

The exit stream has the following composition:

| | |
|---|---|
| dimethylether | 0.40% w. |
| methanol | 8.03% w. |
| acetone | 0.49% w. |
| 2-methoxy-propene | 19.27% w. |
| trimethylborate | 5.58% w. |
| 2,2-dimethoxypropane | 0.05% w. |
| 2,2-dimethyl-1,3-dioxolane | 38.05% w. |
| 2-methoxy-1,3,2-dioxaborolane | 28.13% w. |

Trimethylborate and 2,2-dimethyl-1,3-dioxolane % conversion is 42.54% and 83.5% respectively.

Selectivity in 2-methoxy-propene corresponds to 96.79% of the converted dioxolane.

EXAMPLE 7

After 80 hours running of the same catalyst of the foregoing example, a mixture consisting of:

| | |
|---|---|
| trimethylborate | 61.94% w. |
| 2,2-dimethyl-1,3-dioxolane | 38.06% w. | vaporized at 170° C., is passed through the reactor with a flow rate of 35 g/h. The exit stream has the following composition:

| | |
|---|---|
| dimethylether | 0.19% w. |
| methanol | 2.3% w. |
| acetone | 0.24% w. |
| 2-methoxy-propene | 5.17% w. |
| trimethylborate | 52.95% w. |
| 2,2-dimethoxypropane | 1.09% w. |
| 2,2-dimethyl-1,3-dioxolane | 29.27% w. |
| 2-methoxy-1,3,2-dioxaborolane | 8.79% w. |

Trimethylborate and 2,2-dimethyl-1,3-dioxolane conversion is 14.51% and 23.1% respectively.

Selectivity in 2-methoxy-propene corresponds to 83.3% of the converted dioxolane.

EXAMPLE 8

After 90 hours running of the catalyst of the foregoing example, a mixture consisting of:

| | |
|---|---|
| trimethylborate | 57.08% w. |
| 2,2-dimethyl-1,3-dioxolane | 42.92% w. | vaporized at 220° C., is blown over the catalyst with a flow rate of 40 g/h.

The exit stream has the following composition:

| | |
|---|---|
| dimethylether | 4.47% w. |
| methanol | 5.10% w. |
| acetone | 5.63% w. |
| 2-methoxy-propene | 12.27% w. |
| trimethylborate | 29.24% w. |
| 2,2-dimethoxypropane | 0.47% w. |
| 2,2-dimethyl-1,3-dioxolane | 15.15% w. |
| 2-methoxy-1,3,2-dioxaborolane | 27.67% w. |

Trimethylborate and 2,2-dimethyl-1,3-dioxolane % conversion is 48.77% and 64.70% respectively. Selectivity in 2-methoxy-propene corresponds to 62.61% of the converted dioxolane.

EXAMPLE 9

A diatomaceous earth (100 ml corresponding to 37 g) calcined and grinded in particles of 30÷60 mesh, with a surface area comprised between 4 and 6 m²/g, is charged into a jacketed tubular reactor ($\phi i=1''$; h=25 cm). The operating temperature is brought to 200° C. and a mixture of:

| | |
|---|---|
| trimethylborate | 33.51% w. |
| 2,2-dimethyl-1,3-dioxolane | 66.49% w. | previously vaporized at the same temperature, is continuously blown through the reactor with a flow rate of 30 g/h.

The exit vapor has the following composition:

| | |
|---|---|
| dimethylether | 0.02% w. |
| methanol | 5.67% w. |
| acetone | 0.03% w. |
| 2-methoxy-propene | 12.76% w. |
| trimethylborate | 14.59% w. |
| 2,2-dimethoxypropane | 0.48% w. |
| 2,2-dimethyl-1,3-dioxolane | 47.89% w. |
| 2-methoxy-1,3,2-dioxaborolane | 18.56% w. |

Trimethylborate and 2,2-dimethyl-1,3-dioxolane % conversion is 56.5% and 28% respectively.

Selectivity in 2-methoxy-propene corresponds to 97.2% of the converted dioxolane.

EXAMPLE 10

After 8 hours running of the catalyst described in example 9 under the same reaction conditions, the temperature of the reactor and of the vaporized charge is brought to 200° C. With the same feeding mixture, an effluent having the following composition is collected:

| | |
|---|---|
| dimethylether | 0.03% w. |
| methanol | 6.26% w. |
| acetone | 0.04% w. |
| 2-methoxy-propene | 14.1% w. |

-continued

| | |
|---|---|
| trimethylborate | 12.79% w. |
| 2,2-dimethoxypropane | 0.34% w. |
| 2,2-dimethyl-1,3-dioxolane | 46.12% w. |
| 2-methoxy-1,3,2-dioxaborolane | 20.32% w. |

Trimethylborate and 2,2-dimethyl-1,3-dioxolane % conversion is 61.8% and 30.6% respectively.

Selectivity in 2-methoxy-propene corresponds to 98.1% of the converted dioxolane.

EXAMPLE 11

After 26 hours running, by feeding the same mixture as in the foregoing examples, at a temperature of 250° C. and with a flow rate of 30 g/h, an exit stream with the following composition is obtained:

| | |
|---|---|
| dimethylether | 0.12% w. |
| methanol | 9.13% w. |
| acetone | 0.15% w. |
| 2-methoxy-propene | 20.56% w. |
| trimethylborate | 3.27% w. |
| 2,2-dimethoxypropane | 0.34% w. |
| 2,2-dimethyl-1,3-dioxolane | 36.77% w. |
| 2-methoxy-1,3,2-dioxaborolane | 29.65% w. |

Trimethylborate and 2,2-dimethyl-1,3-dioxolane % conversion is 90.2% and 44.7% respectively.

Selectivity in 2-methoxy-propene corresponds to 98% of the converted dioxolane.

EXAMPLE 12

After 40 hours overall running, blowing a mixture of:

| | |
|---|---|
| trimethylborate | 50.47% w. |
| 2,2-dimethyl-1,3-dioxolane | 49.53% w. | over the same catalyst of the preceding example, at the operating temperature of 250° C. and with a flow rate of 20 g/h, an effluent with the following composition is obtained:

| | |
|---|---|
| dimethylether | 0.17% w. |
| methanol | 10.93% w. |
| acetone | 0.21% w. |
| 2-methoxy-propene | 24.61% w. |
| trimethylborate | 14.34% w. |
| 2,2-dimethoxypropane | 0.29% w. |
| 2,2-dimethyl-1,3-dioxolane | 14.01% w. |
| 2-methoxy-1,3,2-dioxaborolane | 35.44% w. |

Trimethylborate and 2,2-dimethyl-1,3-dioxolane % conversion is 71.6% and 71.7% respectively.

Selectivity in 2-methoxy-propene corresponds to 98.1% of the converted dioxolane.

EXAMPLE 13

After 60 hours overall running of the catalyst of the foregoing examples, a mixture consisting of:

| | |
|---|---|
| methanol | 8.0% w. |
| trimethylborate | 46.3% w. |
| 2,2-dimethyl-1,3-dioxolane | 45.7% w. | is passed through the reactor with a flow rate of 30 g/h, at the operating temperature of 250° C. The effluent which is collected has the following composition:

| | |
|---|---|
| dimethylether | 0.19% w. |
| methanol | 16.63% w. |
| acetone | 0.24% w. |
| 2-methoxy-propene | 19.42% w. |
| trimethylborate | 17.78% w. |
| 2,2-dimethoxypropane | 0.10% w. |
| 2,2-dimethyl-1,3-dioxolane | 17.68% w. |
| 2-methoxy-1,3,2-dioxaborolane | 27.96% w. |

Trimethylborate and 2,2-dimethyl-1,3-dioxolane % conversion is 61.6% and 61.3% respectively.

Selectivity in 2-methoxy-propene corresponds to 98.2% of the converted dioxolane.

EXAMPLE 14

A diatomaceous earth (100 ml corresponding to 37 g) calcined and grinded in particles of 30÷60 mesh, is charged into a jacketed tubular reactor ($\phi i = 1''$; h=25 cm).

The operating temperature is brought to 250° C. and a mixture of:

| | |
|---|---|
| trimethylborate | 42.1% w. |
| 1,4-dioxa-[4,5]spirodecane | 57.9% w. | previously vaporized at the same temperature, is blown from the top to the bottom of the reactor with a flow rate of 30 g/h.

The exit vapor has the following composition:

| | |
|---|---|
| dimethylether | 0.06% w. |
| methanol | 5.07% w. |
| trimethylborate | 25.27% w. |
| cyclohexanone | 0.13% w. |
| 1-methoxy-cyclohexene | 17.71% w. |
| 1,1-dimethoxy-cyclohexane | 0.37% w. |
| 1,4-dioxa-[4,5]-spirodecane | 34.89% w. |
| 2-methoxy-1,3,2-dioxaborolane | 16.50% w. |

Trimethylborate and 1,4-dioxa[4,5]spirodecane % conversion is 40% and 39.7% respectively.

Selectivity in 1-methoxy-cyclohexen corresponds to 99% of the converted 1,4-dioxa[4,5]spirodecane.

EXAMPLE 15

A mixture of:

| | |
|---|---|
| trimethylborate | 53.28% w. |
| 2-methyl-1,3-dioxolane | 46.72% w. | is passed through the same reactor as in the foregoing example, at an operating temperature of 250° C. and a flow rate of 40 g/h.

The effluent which is collected has the following composition:

| | |
|---|---|
| dimethylether | 0.06% w. |
| methanol | 3.55% w. |
| acetaldehyde | 0.06% w. |
| methoxy-ethylene | 6.43% w. |
| trimethylborate | 40.78% w. |
| 1,1-dimethoxyethane | 0.75% w. |
| 2-methyl-1,3-dioxolane | 36.11% w. |

| | |
|---|---|
| -continued | |
| 2-methoxy-1,3,2-dioxaborolane | 12.26% w. |

Trimethylborate and 2-methyl-1,3-dioxolane % conversion is 23.5% and 22% respectively.

Selectivity in methyl vinyl ether corresponds to 91.9% of the converted dioxolane.

EXAMPLE 16

A diatomaceous earth (100 ml corresponding to 37 g) calcined and grinded in particles of 30÷60 mesh, is charged into a jacketed tubular reactor ($\phi$i=1"; h=25 cm).

The temperature is brought to 250° C. and a vaporized mixture of:

| | |
|---|---|
| trimethylborate | 67.6% w. |
| 2-methyl-2-phenyl-1,3-dioxolane | 32.4% w. | pre-heated at the operating temperature, is blown from the top to the bottom of the reactor with a flow rate of 50 ml/h.

The exit stream which is collected has the following composition:

| | |
|---|---|
| dimethylether | 0.05% w. |
| methanol | 2.21% w. |
| trimethylborate | 59.93% w. |
| acetophenone | 0.12% w. |
| 1-methoxy-1-phenyl-ethene | 9.27% w. |
| 1,1-dimethoxy-1-phenyl-ethane | 0.59% w. |
| 2-methyl-2-phenyl-1,3-dioxolane | 20.30% w. |
| 2-methoxy-1,3,2-dioxaborolane | 7.52% w. |

2-Methyl-2-phenyl-1,3-dioxolane conversion is 37.3% and selectivity in 1-methoxy-1-phenyl-ethene is 93.8%.

EXAMPLE 17

After 10 hours running of the catalyst of the foregoing example under the same reaction conditions, flow rate is reduced to 30 ml/h, and the collected exit stream has the following composition:

| | |
|---|---|
| dimethylether | 0.05% w. |
| methanol | 2.85% w. |
| trimethylborate | 57.84% w. |
| acetophenone | 0.12% w. |
| 1-methoxy-1-phenyl-ethene | 11.97% w. |
| 1,1-dimethoxy-1-phenyl-ethane | 0.60% w. |
| 2-methyl-2-phenyl-1,3-dioxolane | 17.00% w. |
| 2-methoxy-1,3,2-dioxaborolane | 9.57% w. |

2-Methyl-2-phenyl-1,3-dioxolane conversion is 47.5% and selectivity in 1-methoxy-1-phenyl-ethene is 95.1%.

EXAMPLE 18

After 20 hours running of the catalyst of example 16, the operating temperature is brought to 270° C. and the flow rate of the vaporized charge is reduced to 30 ml/h.

The exit stream has the following composition:

| | |
|---|---|
| dimethylether | 0.15% w. |
| methanol | 4.01% w. |
| trimethylborate | 53.97% w. |
| acetophenone | 0.40% w. |
| 1-methoxy-1-phenyl-ethene | 16.78% w. |
| 1,1-dimethoxy-1-phenyl-ethane | 0.50% w. |
| 2-methyl-2-phenyl-1,3-dioxolane | 11.12% w. |

| | |
|---|---|
| -continued | |
| 2-methoxy-1,3,2-dioxaborolane | 13.07% w. |

2-Methyl-2-phenyl-1,3-dioxolane conversion is 66% and selectivity in 1-methoxy-1-phenyl-ethene is 95.2%.

EXAMPLE 19

A vaporized mixture of:

| | |
|---|---|
| trimethylborate | 18.9% w. |
| 2-methyl-2-phenyl-1,3-dioxolane | 29.8% w. |
| benzene | 51.3% w. | pre-heated at the operating temperature (250° C.), is passed through the same reactor of the foregoing example with a flow rate of 30 ml/h.

The exit stream which is collected has the following composition

| | |
|---|---|
| methanol | 1.66% w. |
| trimethylborate | 13.37% w. |
| benzene | 51.30% w. |
| 1-methoxy-1-phenyl-ethene | 6.97% w. |
| 1,1-dimethoxy-1-phenyl-ethane | 0.20% w. |
| 2-methyl-2-phenyl-1,3-dioxolane | 21.07% w. |
| 2-methoxy-1,3,2-dioxaborolane | 5.42% w. | b 2-Methyl-2-phenyl-1,3-dioxolane conversion is 29.3% and selectivity in 1-methoxy-1-phenyl-ethene is 97.7%.

EXAMPLE 20

After 10 hours running of the catalyst under the same operating conditions of the foregoing example, the temperature is brought to 270° C. and the collected exit stream has the following composition:

| | |
|---|---|
| dimethylether | 0.06% w. |
| methanol | 2.26% w. |
| trimethylborate | 11.37% w. |
| benzene | 51.30% w. |
| acetophenone | 0.15% w. |
| 1-methoxy-1-phenyl-ethene | 9.54% w. |
| 1,1-dimethoxy-1-phenyl-ethane | 0.02% w. |
| 2-methyl-2-phenyl-1,3-dioxolane | 17.91% w. |
| 2-methoxy-1,3,2-dioxaborolane | 7.39% w. |

2-Methyl-2-phenyl-1,3-dioxolane conversion is 40% and selectivity in 1-methoxy-1-phenyl-ethene is 98.2%.

We claim:

1. A process for preparing a vinyl ether of general formula I

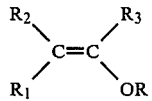

wherein $R_1$ and $R_2$, are selected from the group consisting of hydrogen or a primary, secondary or tertiary alkyl group, $R_3$ is selected from the group consisting of hydrogen, a primary alkyl, phenyl, or phenyl substituted with up to 3 substituents, which may be the same or different, and which are inert toward boric acid esters and permit vaporization of the dioxolane compounds of formula II at a temperature below 400° C., or $R_2$ and $R_3$, taken together, represent a polymethylene chain containing from 3 to 10 carbon atoms wherein one or more hydrogen atoms may be replaced by methyl or ethyl groups, and R is selected from the group consisting of a primary, secondary or tertiary alkyl group, said process comprising reacting a dioxolane compound of formula II

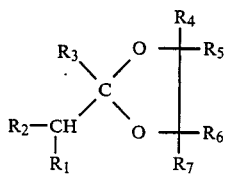

wherein $R_1$, $R_2$, and $R_3$ are as defined above, and $R_4$, $R_5$, $R_6$ and $R_7$, each independently, are selected from the group consisting of hydrogen or an alkyl group, with a boric acid ester of formula III $$B(OR)_3 \qquad \text{III}$$

wherein R is as defined above, in the vapor phase, at a temperature of between 100° and 400° C., and in the presence of a catalyst consisting of acidic oxides.

2. The process of claim 1 wherein the operating temperature is between 180° and 280° C.

3. The process of claim 2 wherein the operating temperature is between 200° and 250° C.

4. The process of claim 1 wherein the catalyst is selected from the group consisting of diatomaceous earth, alumina, boria-alumina, silica, and synthetic or naturally occurring mixtures of silica-alumina in which other oxides may be present.

5. The process of claim 1 wherein the dioxolane-to-boric-acid-ester molar feed ratio is between 10:1 and 0.5:1.

6. The process of claim 5 wherein said molar ratio is between 5:1 and 1:1.

7. The process of claim 1 wherein the reactants are in contact with the catalyst for between 10 and 600 seconds.

8. The process of claim 7 wherein said contact time is between 120 and 240 seconds.

9. The process of claim 1 further comprising adding a carrier to the gaseous mixture of reactants.

10. The process of claim 9 wherein said carrier is selected from low-boiling inert organic compounds and alkanols of the formula ROH wherein R is as defined above.

11. The process of claim 4 wherein the catalyst is selected from alumina and diatomaceous earth.

12. The process of claim 11 wherein said catalysts are activated at temperatures between 200° and 1300° C. prior to their use.

13. The process of claim 1 wherein said catalyst is obtained through wet-coating of said acidic oxide with boric acid.

14. The process of claim 1 wherein $R_4$, $R_5$, $R_6$ and $R_7$ are each hydrogen

* * * * *